United States Patent
Joo et al.

(10) Patent No.: US 9,518,919 B2
(45) Date of Patent: Dec. 13, 2016

(54) APPARATUS AND METHOD FOR MEASURING HEMOGLOBIN CONCENTRATION WITHIN BLOOD USING LIGHT AND HEAT LIGHT SCATTERING

(71) Applicant: INDUSTRY-ACADEMIC COOPERATION FOUNDATION YONSEI UNIVERSITY, Seoul (KR)

(72) Inventors: Chulmin Joo, Goyang-si (KR); Dong Hak Lee, Wonju-si (KR); Ui Han Kim, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/866,410

(22) Filed: Sep. 25, 2015

(65) Prior Publication Data

US 2016/0091423 A1 Mar. 31, 2016

(30) Foreign Application Priority Data

Sep. 26, 2014 (KR) ........................ 10-2014-0129413

(51) Int. Cl.
*G01N 33/48* (2006.01)
*G01N 21/51* (2006.01)
(Continued)

(52) U.S. Cl.
CPC .............. *G01N 21/51* (2013.01); *G01N 33/49* (2013.01); *G06T 7/0012* (2013.01); *G06T 2207/20056* (2013.01); *G06T 2207/30024* (2013.01)

(58) Field of Classification Search
CPC .................. A61B 18/20; A61B 18/203; A61B 2017/00057; F21V 7/00; G01N 21/27; G01N 21/59; G01N 21/75; G01N 2201/061; G01N 2201/06113; G01N 2201/062; G01N 2201/068; G01N 2333/545; G01N 2800/224
See application file for complete search history.

(56) References Cited

U.S. PATENT DOCUMENTS

| 2010/0044570 A1* | 2/2010 | McGill ................... G01N 21/71 250/338.5 |
| 2011/0076199 A1* | 3/2011 | Meller ................. G01N 21/253 422/82.05 |

(Continued)

FOREIGN PATENT DOCUMENTS

| JP | 2010266315 A | 11/2010 |
| KR | 10-2002-0035101 A | 5/2002 |

(Continued)

OTHER PUBLICATIONS

Uihan Kim et al., "Direct Measurement of Hemoglobin Concentrations Using Photo-thermal Angular Scattering", Journal of the Optical Society of Korea, 2014, Seoul, Korea.

*Primary Examiner* — Michael P Stafira
(74) *Attorney, Agent, or Firm* — LRK Patent Law Firm

(57) ABSTRACT

An apparatus for measuring a hemoglobin concentration includes a reference light source unit, a light and heat light source unit configured to emit a light and heat beam for generating a light and heat effect, an accommodation unit configured to accommodate obtained blood samples, an image acquisition unit configured to write a primary pattern formed after the reference beam emitted by the reference light source unit is incident on the accommodation unit and a secondary pattern formed under an influence of a light and heat effect after the light and heat beam emitted by the light and heat light source unit is incident on the accommodation unit, and a concentration calculation unit electrically connected to the image acquisition unit and configured to
(Continued)

calculate a hemoglobin concentration based on a difference between the primary pattern and the secondary pattern.

16 Claims, 4 Drawing Sheets

(51) Int. Cl.
*G06T 7/00* (2006.01)
*G01N 33/49* (2006.01)

(56) References Cited

U.S. PATENT DOCUMENTS

| | | | |
|---|---|---|---|
| 2011/0165595 A1* | 7/2011 | Catanzaro | B01L 7/52 435/7.21 |
| 2011/0271738 A1* | 11/2011 | McGill | G01N 21/64 73/23.41 |
| 2013/0130265 A1* | 5/2013 | Parikh | C12Q 1/686 435/6.12 |

FOREIGN PATENT DOCUMENTS

| | | |
|---|---|---|
| KR | 10-2010-0011133 A | 2/2010 |
| KR | 10-2011-0057341 | 6/2011 |

* cited by examiner

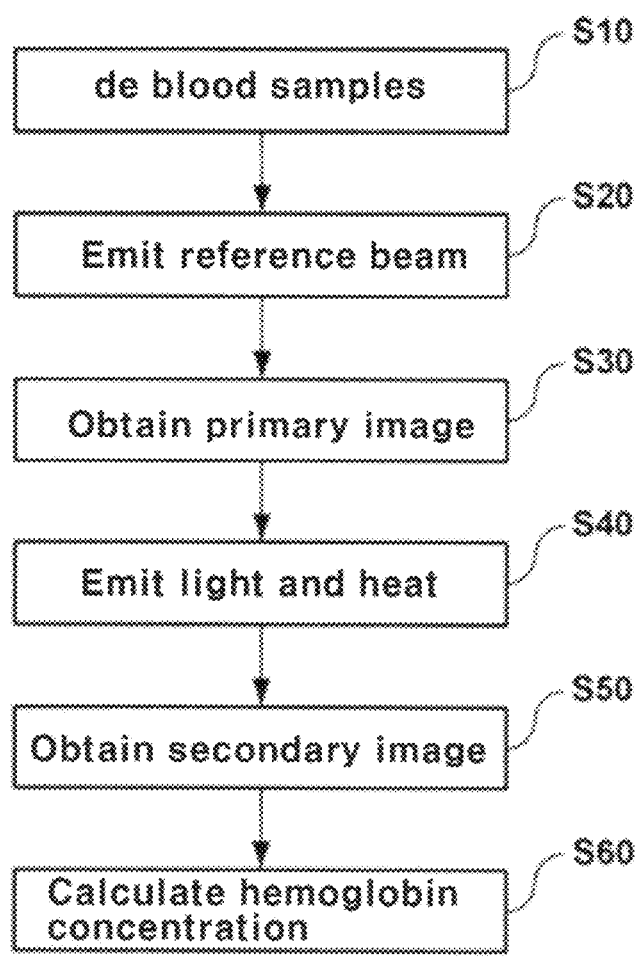

APPARATUS AND METHOD FOR MEASURING HEMOGLOBIN CONCENTRATION WITHIN BLOOD USING LIGHT AND HEAT LIGHT SCATTERING

CROSS REFERENCE TO RELATED APPLICATION

The present application claims the benefit of Korean Patent Application No. 10-2014-0129413 filed in the Korean Intellectual Property Office on Sep. 26, 2014, the entire contents of which are incorporated herein by reference.

BACKGROUND OF THE INVENTION

1. Technical Field

The present invention relates to an apparatus and method for measuring a hemoglobin concentration within blood using light and heat light scattering and, more particularly, to an apparatus and method, which are capable of quantitatively measuring a hemoglobin concentration within blood by measuring a pattern generated when a laser is scanned onto a micro channel including blood and detecting a change of a scattering pattern generated when light and heat stimulus light sources having different wavelengths are simultaneously scanned.

2. Description of the Related Art

Hemoglobin is iron-containing protein present in a red blood cell and is major carriage means of oxygen included in blood. Hemoglobin deficiency leads to an anemia symptom. The cause of anemia is very various. For example, the measurement of a hemoglobin concentration is used for a classification for each cause of anemia. For example, if anemia is generated due to iron deficiency, erythrocyte indices are reduced, but are increased in anemia attributable to vitamin B12 deficiency or folic acid deficiency. Anemia may be generated due to other many causes. It is very important to measure the amount of hemoglobin in first diagnosing and determining anemia because erythrocyte indices have a different aspect for each diagnosis. Furthermore, hemoglobin content is an index sensitive to iron deficiency. Such an index is used to diagnose a disease attributable to iron deficiency or to monitor the effect of iron therapy within the vein.

Various technologies have been developed in order to measure a hemoglobin concentration within blood because hemoglobin content may be used to diagnose several diseases as described above. A technology that is a standard for the measurement of a hemoglobin concentration is to break the lipidic bilayer of hemoglobin using potassium cyanide (KCN) and perform a colorimetric analysis. However, there is a problem in that toxic chemical must be used whenever a hemoglobin concentration is measured. In addition such a method, an electrochemical method and an immunoassay method are suggested. Such methods are problematic in that modeling dependency is high or accuracy is low, an additional sensor using a microelectromechanical system (MEMS) or electrochemistry must be fabricated, and a lot of time is taken to measure a concentration.

SUMMARY OF THE INVENTION

Embodiments of the present invention are directed to measuring a hemoglobin concentration without adding chemicals through a simple configuration including a reference light source unit configured to emit a reference beam, a light and heat light source unit configured to emit a light and heat beam for generating light and heat effect, and a cuvette unit configured to accommodate an obtained blood samples.

Furthermore, embodiments of the present invention are directed to accurately measuring a hemoglobin concentration based on an associative relation between the hemoglobin concentration and a first measurement value by forming the graphs of primary and secondary scattering patterns using the concentration calculation unit and obtaining the first measurement value by performing Fourier transform on a phase shift (or the degree of a phase shift) graph over given time.

An apparatus for measuring a hemoglobin concentration in accordance with an embodiment of the present invention includes a reference light source unit, a light and heat light source unit configured to emit a light and heat beam for generating a light and heat effect, an accommodation unit configured to accommodate obtained blood samples, an image acquisition unit configured to write a primary pattern formed after the reference beam emitted by the reference light source unit is incident on the accommodation unit and a secondary pattern formed under an influence of a light and heat effect after the light and heat beam emitted by the light and heat light source unit is incident on the accommodation unit, and a concentration calculation unit electrically connected to the image acquisition unit and configured to calculate a hemoglobin concentration based on a difference between the primary pattern and the secondary pattern.

A method for measuring a hemoglobin concentration in accordance with an embodiment of the present invention includes providing blood samples to the cuvette unit, emitting, by the reference light source unit, a reference beam, making the emitted reference beam incident on the cuvette unit and obtaining a primary scattering pattern, emitting, by the light and heat light source unit, a light and heat beam, making the emitted light and heat beam incident on the cuvette unit and obtaining a secondary scattering pattern, and calculating a hemoglobin concentration using the primary and secondary scattering patterns.

Furthermore, the wavelength of the reference beam includes a first wavelength region not absorbed by hemoglobin, and wherein the second wavelength region is 300 nm to 600 nm.

Furthermore, the reference light source unit 100 includes any one of a laser, a laser diode and an LED.

The light and heat light source unit 200 includes any one of a diode pumped solid state (DPSS) laser, an LED, and a laser diode.

The accommodation unit 300 is made of a transparent material so that the light and heat beam is transferred to blood.

Furthermore, the image acquisition unit 400 includes any one of a complementary metal-oxide semiconductor (CMOS), a charge coupled apparatus (CCD), a single photodiode, a photodiode array, and a position sensitive detector.

Furthermore, the light and heat beam emitted by the light and heat light source unit is changed into a thick and parallel pencil of rays through a beam expander before the light and heat beam is incident on the accommodation unit.

A concave lens is placed disposed between the accommodation unit and the image acquisition unit, and expanded primary and secondary scattering patterns are written in the image acquisition unit.

Furthermore, the light and heat beam includes a beam having intensity varied over time.

Furthermore, the concentration calculation unit 500 forms the graphs of the primary and secondary patterns, obtains the first measurement value of a peak by performing Fourier transform on the graph of a phase shift over given time, and calculates a hemoglobin concentration based on an associative relation between a hemoglobin concentration and the first measurement value.

An apparatus for measuring a hemoglobin concentration may be configured to include a reference light source unit 100, a light and heat light source unit 200 configured to emit a light and heat beam for generating a light and heat effect, an accommodation unit 300 configured to accommodate obtained blood samples, an image acquisition unit 400 configured to write a primary pattern formed after the reference beam emitted by the reference light source unit 100 is incident on the accommodation unit 300 and a secondary pattern formed under an influence of a light and heat effect after the light and heat beam emitted by the light and heat light source unit 200 is incident on the accommodation unit 300, and a concentration calculation unit 500 electrically connected to the image acquisition unit and configured to calculate a hemoglobin concentration based on a difference between the primary pattern and the secondary pattern.

The wavelength of the reference beam may include a first wavelength region which is a wavelength region in which hemoglobin is less absorbed compared to the light and heat beam. In some embodiments, the first wavelength region may be 600 nm to 1100 nm.

The wavelength of the light and heat beam may include a second wavelength region absorbed by hemoglobin. In some embodiments, the second wavelength region may be 300 nm to 600 nm.

The accommodation unit 300 may include a transparent portion generally or partially so that the light and heat beam may be transferred to the blood.

The image acquisition unit 400 may include any one of a complementary metal-oxide semiconductor (CMOS), a charge coupled apparatus (CCD), a single photodiode, a photodiode array, and a position sensitive detector.

The light and heat beam emitted by the light and heat light source unit may be changed into a thick and parallel pencil of rays through a beam expander before the light and heat beam may be incident on the accommodation unit.

The apparatus may further include a concave lens disposed between the accommodation unit and the image acquisition unit so that expanded primary and secondary scattering patterns are written in the image acquisition unit.

The light and heat beam may include a beam having intensity varied over time.

The concentration calculation unit 500 may form the graphs of the primary and secondary patterns, obtains the first measurement value of a peak by performing Fourier transform on the graph of a phase shift over given time, and calculates a hemoglobin concentration based on an associative relation between a hemoglobin concentration and the first measurement value. The difference between the primary pattern and the secondary pattern may include a phase shift.

The apparatus for measuring a hemoglobin concentration according to the present embodiment may be configured to include a tube inserted into the apparatus for measuring a hemoglobin concentration and configured to accommodate blood samples.

In a tube inserted into an apparatus for measuring a hemoglobin concentration and configured to accommodate blood samples in accordance with an embodiment of the present invention, the tube may be inserted into the apparatus for measuring a hemoglobin concentration which may include a reference light source unit, a light and heat light source unit, and an image acquisition unit and disposed adjacent to the reference light source unit, the light and heat light source unit, and the image acquisition unit. The tube may be provided so that blood samples exposed to a reference beam emitted by the reference light source unit and accommodated in the tube generate a primary pattern. The tube may be provided so that blood samples exposed to a light and heat beam emitted by the light and heat light source unit generates a secondary pattern through a light and heat effect. The tube may be configured to accommodate blood samples so that the image acquisition unit calculates a hemoglobin concentration by measuring a difference between the first pattern and the second pattern.

BRIEF DESCRIPTION OF THE DRAWINGS

FIG. 5 is a flowchart illustrating a method for measuring a hemoglobin concentration in accordance with an embodiment of the present invention.

DETAILED DESCRIPTION

Hereinafter, some embodiments of the present invention are described in detail with reference to the accompanying drawings. Prior to the description, terms or words used in this specification and the claims should not be limitedly interpreted as having common meanings or those found in dictionaries, but should be interpreted as having meanings and concepts which comply with the technical spirit of the present invention.

In the entire specification, unless explicitly described to the contrary, the word "include, have, or comprise" will be understood to imply the inclusion of stated elements but not the exclusion of any other elements.

In each of steps, symbols are used for convenience of description, and the symbols do not describe order of the steps. The steps may be performed in order different from order described in the context unless specific order is clearly described in the context. That is, the steps may be performed according to described order, may be performed substantially at the same time, or may be performed in reverse order.

Figure 1:
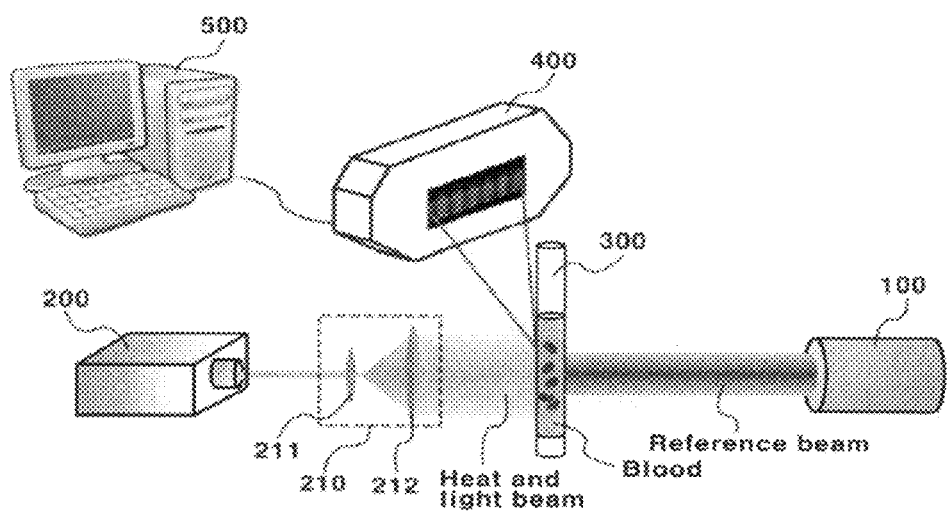
FIG. 1 is a configuration diagram showing an apparatus for measuring a hemoglobin concentration in accordance with an embodiment of the present invention.

FIG. 1 is a configuration diagram showing an apparatus for measuring a hemoglobin concentration in accordance with an embodiment of the present invention.

The apparatus for measuring a hemoglobin concentration in accordance with an embodiment of the present invention includes a reference light source unit 100 configured to emit a reference beam for generating a primary scattering pattern, a light and heat light source unit 200 configured to emit a light and heat beam for generating a light and heat effect, a cuvette unit 300 configured to accommodate obtained blood samples, an image acquisition unit 400 configured to write the signal of a primary scattering pattern formed after a reference beam emitted by the reference light source unit 100 is incident on the cuvette unit 300 and the signal of a secondary scattering pattern formed under the influence of a light and heat effect after a light and heat beam emitted by the light and heat light source unit 200 is incident on the cuvette unit 300, and a concentration calculation unit 500 electrically connected to the image acquisition unit 400 and configured to calculate a hemoglobin concentration by measuring the phase shift of a secondary scattering pattern that has been formed into a graph from a primary scattering pattern of a graph form.

The reference light source unit 100 emits a reference beam in order to generate a primary scattering pattern. The reference light source unit 100 may include various types of light sources and may be a laser or a laser diode. Furthermore, the reference beam may have a wavelength of 600 nm to 1100 nm.

A reference beam emitted by the reference light source unit 100 is incident on the cuvette unit 300 in which obtained blood samples have been accommodated. The cuvette unit 300 is made of a transparent material so that the reference beam and the light and heat beam are transferred to blood. When the reference beam is incident on the cuvette unit 300, a primary scattering pattern is formed on the side opposite the reference light source unit 100 on the basis of the cuvette unit 300. The primary scattering pattern may have a different size or interval depending on the refractive index and diameter of the cuvette unit 300. The formed primary scattering pattern is written by the image acquisition unit 400 in the form of an electrical signal. Furthermore, a concave lens may be placed between the cuvette unit 300 and the image acquisition unit 400 so that a scattering pattern is enlarged and written in the image acquisition unit 400.

The image acquisition unit 400 may be a two-dimensional image acquisition device. More specifically, the image acquisition unit 400 may be any one of a complementary metal-oxide semiconductor (CMOS), a charge coupled apparatus (CCD), a single photodiode, a photodiode array, and a position sensitive detector.

The light and heat light source unit 200 emits a light and heat beam in order to generate a secondary scattering pattern. The light and heat light source unit 200 may include various types of light sources and may be any one of a diode pumped solid state (DPSS) a laser, LED, and a laser diode. Furthermore, the light and heat beam may have a wavelength of 300 nm to 600 nm. Furthermore, the light and heat beam emitted by the light and heat light source unit 200 may be converted into a pencil of rays that is thick and parallel through a beam expander 210 before it is incident on the cuvette unit 300. The beam expander 210 may include two first and second lenses 211 and 212.

The light and heat beam emitted by the light and heat light source unit 200 is absorbed by obtained blood samples through the cuvette unit 300. Hemoglobin forming red blood cells absorbs the light and heat beam and emits the absorbed beam in a thermal energy form. The temperature of surrounding blood samples is increased due to the emitted thermal energy and the refractive indices f the blood samples are changed, thereby forming a secondary scattering pattern shifted in the length direction of the pattern. The formed secondary scattering pattern is written by the image acquisition unit 400 in the form of an electrical signal.

In addition, the reference light source unit 100 and the light and heat light source unit 200 have been illustrated as being separated, but may form an integration module. In this case, the integration module may emit beams having wavelengths of different regions.

Figure 2:
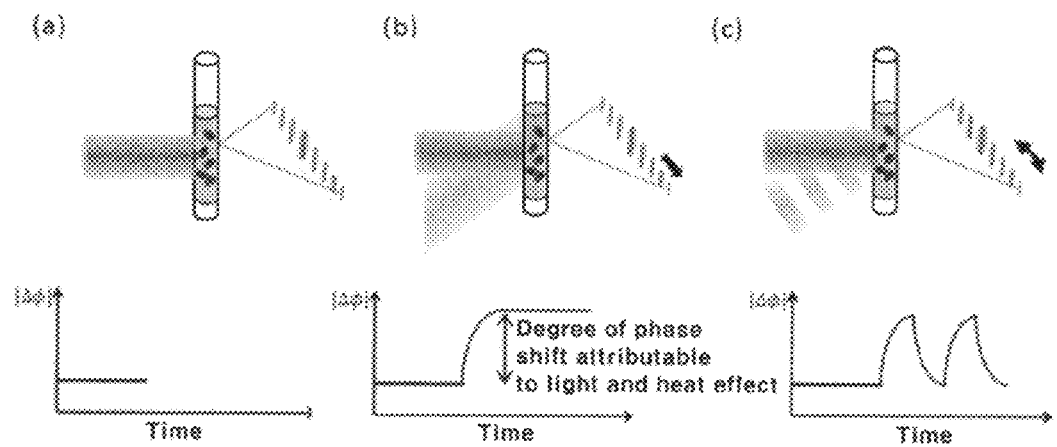
FIG. 2 shows that a scattering pattern of hemoglobin is shifted by a light and heat effect.

FIG. 2 shows that a scattering pattern of hemoglobin is shifted by a light and heat effect.

FIG. 2(a) shows a phase shift $|\Delta\phi|$ according to a primary scattering pattern formed when only a reference beam is incident on the cuvette unit 300 over time. FIG. 2(b) shows a phase shift $|\Delta\phi|$ according to a secondary scattering pattern shifted in the length direction of the pattern when a light and heat beam is incident on the cuvette unit 300 along with the reference beam already incident on the cuvette unit 300 over time. FIG. 2(c) shows a phase shift $|\Delta\phi|$ according to a scattering pattern when an intensity-modulated light and heat beam is incident over time. In this case, the graph of the phase shift $|\Delta\phi|$ over time has a form which is vibrated at a constant cycle in response to the frequency of the intensity-modulated light and heat beam.

Figure 3:
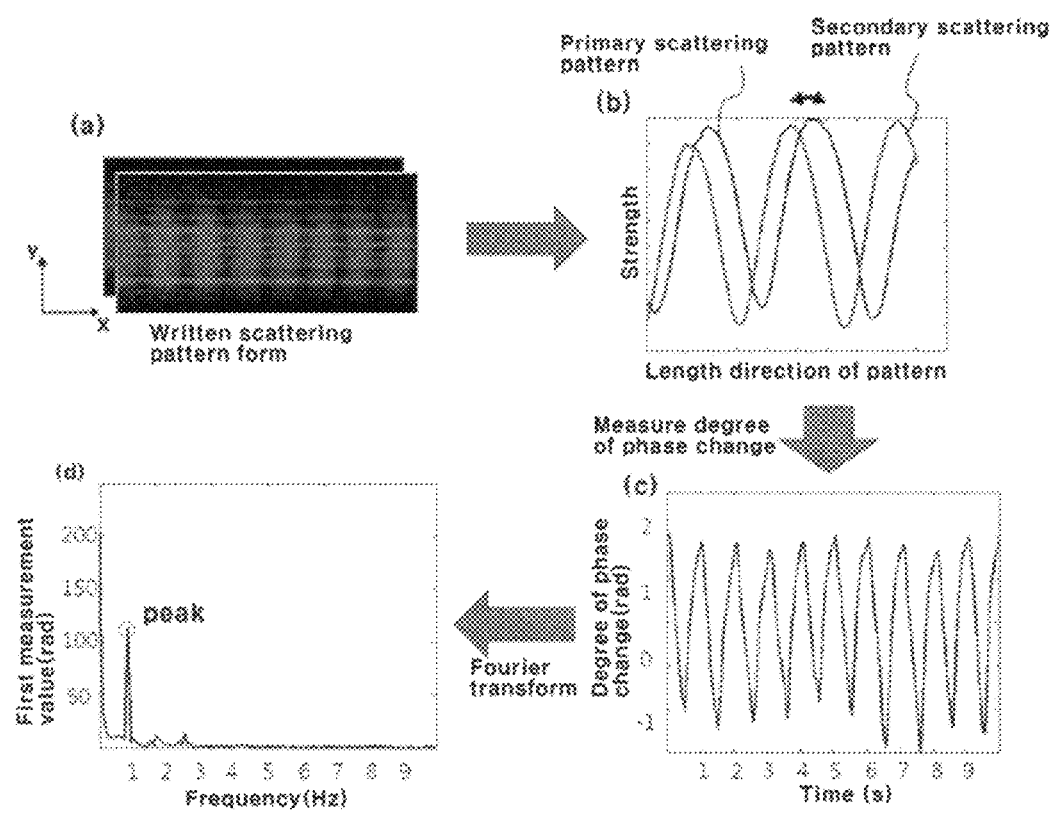
FIG. 3 illustrates a process of measuring a phase shift of a secondary scattering pattern which has been shifted into a graph from a primary scattering pattern of a graph form and a first measurement value in the concentration calculation unit of the apparatus for measuring a hemoglobin concentration in accordance with an embodiment of the present invention.
Figure 4:
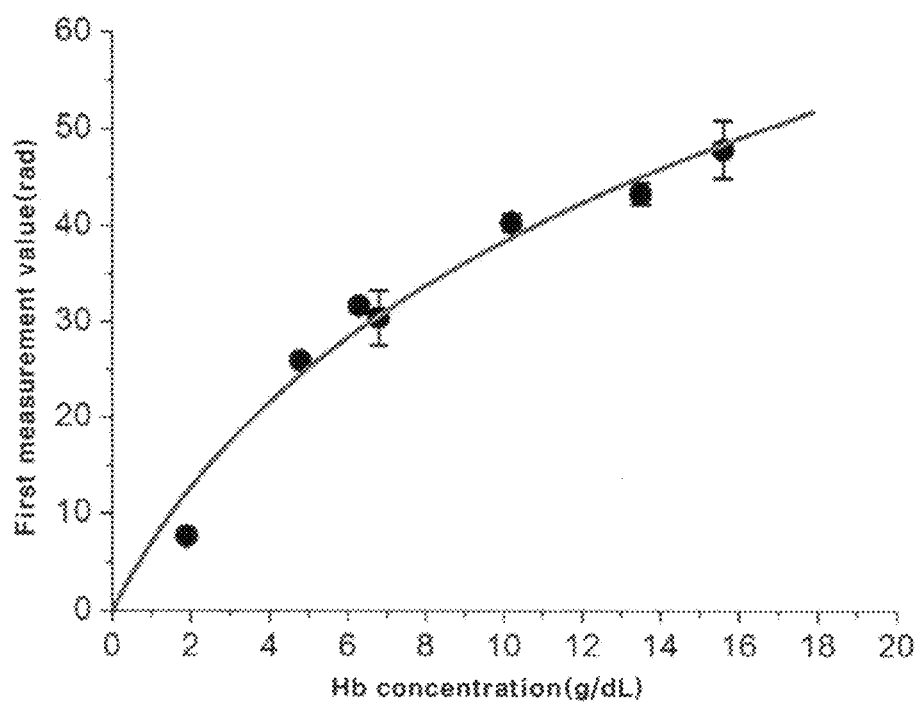
FIG. 4 is a graph showing an associative relation between a first measurement value and a hemoglobin concentration measured by the concentration calculation unit.

In descriptions regarding FIGS. 3 and 4, the light and heat beam is meant to include the intensity-modulated light and heat.

FIG. 3 illustrates a process of measuring a phase shift of a secondary scattering pattern which has been changed into a graph from a primary scattering pattern of a graph form and a first measurement value in the concentration calculation unit of the apparatus for measuring a hemoglobin concentration in accordance with an embodiment of the present invention.

As shown in FIG. 3(a), the primary and secondary scattering patterns are written in the image acquisition unit 400 in a two-dimensional image form. In the image, the length direction of the pattern corresponds to the x axis, and the height direction of the pattern corresponds to the y axis. FIG. 3(b) shows the graph of a scattering pattern having an image form. More specifically, FIG. 3(b) shows that the scattering pattern written in a two-dimensional image form in FIG. 3(a) is averaged in the y axis direction and formed into a graph in a one-dimensional way.

In the graph of FIG. 3(b), the x axis denotes the length direction of the pattern, and the y axis denotes the intensity of light detected by the image acquisition unit 400. A graph indicated by blue denotes the primary scattering pattern, and a graph indicated by red denotes the secondary scattering pattern. If an intensity-modulated light and heat beam is used, the secondary scattering pattern is vibrated left and right over time. The secondary scattering pattern of FIG. 3(b) shows that the secondary scattering pattern has been shifted from the primary scattering pattern in the x-axis direction to the maximum extent.

FIG. 3(c) shows a phase shift over time. When an intensity-modulated light and heat beam is incident, a phase shift $|\Delta\phi|$ over time has a generally vibrating form. Furthermore, FIG. 3(c) shows a form with which graphs having various frequencies have been merged. Accordingly, Fourier transform is performed in order to obtain the amplitude value of a graph corresponding to the frequency of the intensity-modulated light and heat beam.

FIG. 3(d) is a graph showing that a phase shift graph over time has been subjected to Fourier transform. In FIG. 3(d), the x axis denotes a frequency, and the y axis denotes a first measurement value. The first measurement value is obtained by performing Fourier transform on the phase shift (or the degree of a phase shift) over time and means F(w) in Equation 1 below. ω denotes a frequency, f(t) denotes a phase shift graph (FIG. 3c) over time, j is an imaginary number, and t is time (s).

$$\Gamma(\omega) = |\int_{-m}^{n} f(t) e^{-j\omega t} dt| \quad (1)$$

In FIG. 3(d), a peak means a point having the greatest y-axis value. In the peak, the y-axis value means an F value corresponding to the frequency of the intensity-modulated light and heat beam in the graph of FIG. 3(c).

FIG. 4 is a graph showing an associative relation between a first measurement value and a hemoglobin concentration measured by the concentration calculation unit.

The degree of a light and heat effect generated in blood samples is changed depending on a hemoglobin concentration. This changes the amplitude of the phase shift graph (refer to FIG. 3c) over time. As a result, this affects the first measurement value of a peak value after Fourier transform. First measurement values measured depending on hemoglobin concentrations g/dL are shown in FIG. 4. In FIG. 4, a red graph shows that the curve of hemoglobin concentrations and first measurement values of peaks have been fit and is represented by Equation 2 below.

$$y = 29.1 * \ln(0.2742x + 1) \quad (2)$$

In Equation 2, y denotes the first measurement value of a peak, and x denotes a hemoglobin concentration g/dL. The fit curve has the best fitting performance when a hemoglobin concentration is 0.1 to 20 g/dL. An associative relation between the first measurement value of a peak and a hemoglobin concentration in accordance with an embodiment of the present invention is not limited to Equation 2. Equation 2 may be influenced by the materials or diameter of the cuvette unit 300.

Furthermore, since a first measurement value is influenced by the intensity of a light and heat beam, a curve may be fit under the same light and heat beam intensity and an unknown hemoglobin concentration may be measured.

After an associative relation between the first measurement value of a peak and a hemoglobin concentration is obtained, a hemoglobin concentration of unknown blood samples may be measured without using chemicals.

FIG. 5 is a flowchart illustrating a method for measuring a hemoglobin concentration in accordance with an embodiment of the present invention.

Referring to FIG. 5, the method for measuring a hemoglobin concentration in accordance with an embodiment of the present invention includes providing blood samples to the cuvette unit 300 at step S10, emitting, by the reference light source unit 100, a reference beam at step S20, making the emitted reference beam incident on the cuvette unit 300 and obtaining a primary scattering pattern at step S30, emitting, by the light and heat light source unit 200, a light and heat beam at step S40, making the emitted light and heat beam incident on the cuvette unit 300 and obtaining a secondary scattering pattern at step S50, and calculating a hemoglobin concentration using the primary and secondary scattering patterns at step S60.

In accordance with embodiments of the present invention, a hemoglobin concentration can be measured without adding chemicals through a simple configuration including the reference light source unit configured to emit a reference beam, the light and heat light source unit configured to emit a light and heat beam for generating a light and heat effect, and the cuvette unit configured to accommodate an obtained blood samples.

Furthermore, a hemoglobin concentration can be accurately measured based on an associative relation between a hemoglobin concentration and a first measurement value by forming the graphs of primary and secondary scattering patterns using the concentration calculation unit and obtaining the first measurement value by performing Fourier transform on a phase shift (or the degree of a phase shift) graph over given time.

The present invention is not limited to the aforementioned specific embodiments and descriptions, and those skilled in the art to which the present invention pertains may modify the present invention in various ways without departing from the gist of the present invention written in the claims. Such modified embodiments fall within the scope of the present invention.

What is claimed is:

1. An apparatus for measuring a hemoglobin concentration, comprising:
    a reference light source unit (100);
    a light and heat light source unit (200) configured to emit a light and heat beam for generating a light and heat effect;
    an accommodation unit (300) configured to accommodate obtained blood samples;
    an image acquisition unit (400) configured to write a primary pattern formed after the reference beam emitted by the reference light source unit (100) is incident on the accommodation unit (300) and a secondary pattern formed under an influence of a light and heat effect after the light and heat beam emitted by the light and heat light source unit (200) is incident on the accommodation unit (300); and
    a concentration calculation unit (500) electrically connected to the image acquisition unit and configured to calculate a hemoglobin concentration based on a difference between the primary pattern and the secondary pattern.

2. The apparatus of claim 1, wherein a wavelength of the reference beam comprises a first wavelength region which is a wavelength region in which hemoglobin is less absorbed compared to the light and heat beam.

3. The apparatus of claim 2, wherein the first wavelength region is 600 nm to 1100 nm.

4. The apparatus of claim 1, wherein a wavelength of the light and heat beam comprises a second wavelength region absorbed by hemoglobin.

5. The apparatus of claim 4, wherein the second wavelength region is 300 nm to 600 nm.

6. The apparatus of claim 1, wherein the reference light source unit (100) comprises any one of a laser, a laser diode and an LED.

7. The apparatus of claim 1, wherein the light and heat light source unit (200) comprises any one of a diode pumped solid state (DPSS) laser, an LED, and a laser diode.

8. The apparatus of claim 1, wherein the accommodation unit (300) comprises a transparent portion generally or partially so that the light and heat beam is transferred to the blood.

9. The apparatus of claim 1, wherein the image acquisition unit (400) comprises any one of a complementary metal-oxide semiconductor (CMOS), a charge coupled apparatus (CCD), a single photodiode, a photodiode array, and a position sensitive detector.

10. The apparatus of claim 1, wherein the light and heat beam emitted by the light and heat light source unit is changed into a thick and parallel pencil of rays through a beam expander before the light and heat beam is incident on the accommodation unit.

11. The apparatus of claim 1, further comprising a concave lens disposed between the accommodation unit and the image acquisition unit so that expanded primary and secondary scattering patterns are written in the image acquisition unit.

12. The apparatus of claim 1, wherein the light and heat beam comprises a beam having intensity varied over time.

13. The apparatus of claim 12, wherein the concentration calculation unit (500) forms graphs of the primary and secondary patterns, obtains a first measurement value of a peak by performing Fourier transform on a graph of a phase shift over given time, and calculates a hemoglobin concentration based on an associative relation between a hemoglobin concentration and the first measurement value.

14. The apparatus of claim 1, wherein the difference between the primary pattern and the secondary pattern comprises a phase shift.

15. The apparatus of claim 1, further comprising a tube configured to have the obtained blood samples accommodated in the tube and detachably coupled to the accommodation unit.

16. A tube inserted into an apparatus for measuring a hemoglobin concentration and configured to accommodate blood samples, wherein:
the tube is inserted into the apparatus for measuring a hemoglobin concentration which comprises a reference light source unit, a light and heat light source unit, and an image acquisition unit and disposed adjacent to the reference light source unit, the light and heat light source unit, and the image acquisition unit,
the tube is provided so that blood samples exposed to a reference beam emitted by the reference light source unit and accommodated in the tube generate a primary pattern,
the tube is provided so that blood samples exposed to a light and heat beam emitted by the light and heat light source unit generates a secondary pattern through a light and heat effect, and
the tube is configured to accommodate blood samples so that the image acquisition unit calculates a hemoglobin concentration by measuring a difference between the first pattern and the second pattern.

* * * * *